(12) United States Patent
Shagdar et al.

(10) Patent No.: US 10,463,691 B2
(45) Date of Patent: Nov. 5, 2019

(54) NATURAL COMPOSITIONS CONTAINING EGGSHELL CALCIUM, ORGANIC HONEY AND LEMON

(71) Applicants: Jargalsaikhan Shagdar, Ulaanbaatar (MN); Odonchimeg Myagmar, Ulaanbaatar (MN)

(72) Inventors: Jargalsaikhan Shagdar, Ulaanbaatar (MN); Odonchimeg Myagmar, Ulaanbaatar (MN)

( * ) Notice: Subject to any disclaimer, the term of this patent is extended or adjusted under 35 U.S.C. 154(b) by 0 days.

(21) Appl. No.: 15/498,541

(22) Filed: Apr. 27, 2017

(65) Prior Publication Data
US 2017/0266225 A1 Sep. 21, 2017

(51) Int. Cl.

| | |
|---|---|
| *A61K 33/06* | (2006.01) |
| *A61K 35/644* | (2015.01) |
| *A61K 36/752* | (2006.01) |
| *A23L 2/52* | (2006.01) |
| *A23G 3/36* | (2006.01) |
| *A23L 7/126* | (2016.01) |
| *A61K 35/57* | (2015.01) |
| *A23C 9/13* | (2006.01) |
| *A23C 11/10* | (2006.01) |
| *A23G 3/42* | (2006.01) |
| *A23G 3/48* | (2006.01) |
| *A21D 2/02* | (2006.01) |
| *A21D 2/34* | (2006.01) |
| *A21D 2/36* | (2006.01) |
| *A23L 33/16* | (2016.01) |
| *A23L 2/39* | (2006.01) |
| *A61K 9/00* | (2006.01) |
| *A61K 9/20* | (2006.01) |

(52) U.S. Cl.
CPC ............... *A61K 33/06* (2013.01); *A21D 2/02* (2013.01); *A21D 2/34* (2013.01); *A21D 2/36* (2013.01); *A23C 9/1307* (2013.01); *A23C 9/1322* (2013.01); *A23C 11/103* (2013.01); *A23G 3/36* (2013.01); *A23G 3/362* (2013.01); *A23G 3/364* (2013.01); *A23G 3/42* (2013.01); *A23G 3/48* (2013.01); *A23L 2/39* (2013.01); *A23L 2/52* (2013.01); *A23L 7/126* (2016.08); *A23L 33/16* (2016.08); *A61K 35/57* (2013.01); *A61K 35/644* (2013.01); *A61K 36/752* (2013.01); *A23V 2002/00* (2013.01); *A61K 9/0095* (2013.01); *A61K 9/2004* (2013.01)

(58) Field of Classification Search
CPC ...... A61K 33/06; A61K 35/57; A61K 36/752; A61K 35/644; A23V 2200/306; A23V 2250/1578; A23L 33/16; A23L 7/126
See application file for complete search history.

(56) References Cited

U.S. PATENT DOCUMENTS

| | | | | |
|---|---|---|---|---|
| 605,190 | A | * | 6/1898 | Sellnnan |
| 2005/0069608 | A1 | * | 3/2005 | Hendricks ............. A23G 3/362 426/74 |

FOREIGN PATENT DOCUMENTS

| | | | | |
|---|---|---|---|---|
| GB | 2449942 | * | 12/2008 | ............ A61K 33/06 |
| SK | 482013 | * | 3/2013 | ............... A61K 9/00 |

OTHER PUBLICATIONS

Green Earth Organics (How many lemons in a pound? May 19, 2015 accessed via http://greenearthorganics.blogspot.com/2015/05/how-many-lemons-in-pound.html on Jan. 3, 2019.*
Brun et al. ("Chicken eggshell as suitable calcium source at home." Int. J. Food Sci. Nutr. 2013, 64(6): 740-3, published on-line Apr. 22, 2013, abstract only).*
Brun et al. ("Chicken eggshell as suitable calcium source at home." Int. J. Food Sci. Nutr. 2013, 64(6): 740-3, published on-line Apr. 22, 2013, full text).*
Chemical and Functional Properties of Food Saccharides (edited by Piotr Tomasik © 2003, Talor & Francis Group Boca Raton, FL 33487 p. 72).*
SK 482013 machine translation, underlying document published Mar. 13, 2013.*

* cited by examiner

*Primary Examiner* — Kortney L. Klinkel

(57) ABSTRACT

The present invention discloses compositions and edible orally delivered products, such as candies, beverages, nutritional bars and dietary supplements that increase bone growth and treat age-related bone loss in humans. The major component of the invention is biological calcium which is derived from natural eggshell powder. The compositions also include organic honey and lemon.

20 Claims, No Drawings

NATURAL COMPOSITIONS CONTAINING EGGSHELL CALCIUM, ORGANIC HONEY AND LEMON

BACKGROUND TO THE INVENTION

1. Field of the Invention

The present invention relates generally to pharmaceutical and nutritional compositions and food additives, and more particularly, to a special blend of eggshell calcium and other ingredients designed to individuals with calcium necessary and/or deficiency for maintaining healthy bone and/or for treating or reducing risk of medical disorder associated with calcium deficiency and/or bone loss related symptoms such as osteoporosis.

2. Description of the Related Art

Approximately 99% of the calcium in the human body is found in the bones and teeth. Therefore, dietary calcium intake has an important impact on bone metabolism and bone health. However, dietary requirements for calcium are determined by the needs for bone development and maintenance, which vary throughout the life stage, with greater needs during the periods of rapid growth in childhood and adolescence, during pregnancy and lactation, and in later life. It is vital, nevertheless, that adequate dietary calcium is consumed at all stages of life—in early life so that the genetically programmed peak bone mass can be reached and in later adulthood so that the skeletal mass can be maintained and age-related bone loss minimized. (Cashman K. D. '*Calcium intake, calcium bioavailability and bone health*', abstract, The British Journal of Nutrition. 2002 May; 87 Suppl 2: S169-77.) Unfortunately, there is evidence that many individuals are not consuming their recommended levels.

Calcium occurs naturally in certain foods. Dairy products such as milk and cheese, for example, are well-known sources of calcium. Some vegetable sources include seaweeds, nuts and seeds, beans and some dark green leafy vegetables also provide significant amounts of calcium, as do some fortified cereals and juices. Tofu made with calcium salts is a good source of calcium, as are canned sardines and canned salmon with edible bones.

According to the recommendation of the Food and Nutrition Board (FNB), the daily calcium intake amount which is required for bone health and to maintain adequate rates of calcium retention in healthy people, ranges from 700 mg (1 to 3 years old child) to 1300 mg (teens and young pregnant and lactating women). However, people never can get sufficient calcium from their food. For instance, if teens drink 3 cups of milk daily, they can get most of their daily calcium, but they still need additional calcium (400 mg more) to get the entire 1300 mg that is necessary for strong bone growth. See *Dietary supplement fact sheets: Calcium*, Office of Dietary Supplements, National Institutes of Health. (2011)

So that to combat this insufficiency, many calcium-containing compounds and vitamin compositions have long been used in the art in various forms, either alone or as ingredients in blend of nutritional supplements and/or food and beverage. Many commercial preparations are also available, typically containing calcium carbonate or calcium phosphate. Other calcium salts have also been described for use in calcium supplements, including calcium lactate, calcium citrate and calcium gluconate.

For example, U.S. Pat. No. 5,698,222 issued to Mazer et al., (December 1997) describes a calcium supplement in solid form containing glycerophosphate, vitamin D and vitamin C.

U.S. Pat. No. 6,106,874 issued to Liebrecht and Philips (August 2000) describes calcium fortified beverage that utilizes a source of calcium from natural milk mineral, calcium lactate gluconate and mixture thereof.

US Patent. 20070264329 issued to Stotler et al (November 2007) describes calcium compositions comprising calcium carbonate and processes for making such compositions in a form of a smaller tablet.

EP 0208362 issued to the Procter & Gamble Company (January 1987) describes a dietary calcium and iron supplement.

WO 1992019251 issued to the Procter & Gamble Company (November 1992) describes nutritional mineral supplements comprising calcium citrate malate and vitamin D.

WO 1992021355 issued to the Procter & Gamble Company (December 1992) describes nutritional mineral supplements comprising calcium citrate malate, salts of manganese, copper and zinc, vitamin D and drug therapies consisting of calcitonin, editronate, diphosphonates and amino-diphosphonates.

WO 2014177876 issued to Green (November 2014) describes a calcium supplement comprises organic calcium salt.

Apart from those mentioned above, one of overlooked sources of calcium is eggshell calcium. However, some US patents and international publications disclosed methods of using eggshell powder to producing various products. Particularly, US Pat. 20140323616 issued to Yongcheng Liu et al., (October 2014) disclosed the method of manufacturing eggshell powder for use in the production of a variety of commercial plastic products. While Chinese publication No. CN 103238643 disclosed a method of bio flour calcium nutrition supplements containing eggshell powder.

Eggshell calcium has as much as 38% of calcium and low phosphorus content. (Masuda "Hen's eggshell calcium." *Clinical calcium,* 2005 January; 15(1): 95-100.) Modern research found that the main component of the eggshell is biological calcium carbonate, about 90% of organic matter 3.55 to 6.45 percent, magnesium carbonate, calcium phosphate 2.5%, lysozyme-rich, bone collagen, keratin, chondroitin sulfate, hyaluronic acid and the like. And it also contains many trace elements such as zinc, copper, manganese, iron, selenium, etc., in which the harmful heavy metal elements such as lead (Pb), arsenic (As) is extremely low, less than 1 ppm. See US Pat. 20060165846 issued to Vladimir Vlad, July 2006, as well as Chinese publication No. CN 103238643, September 2014

Further, clinical studies in postmenopausal women and women with senile osteoporosis showed that eggshell powder reduces pain and osteoresorption and increases mobility and bone density or arrest its loss. The bioavailability of calcium from this source, as tested in piglets, was similar or better than that of food grade purified calcium carbonate. Clinical and experimental studies showed that eggshell powder has positive effects on bone and cartilage and that it is suitable in the prevention and treatment of osteoporosis. See Rovensky, J. et al., "Eggshell calcium in the prevention and treatment of osteoporosis." *International Journal of Clinical Pharmocology Research,* 2003; 23(2-3): 83-92.

Honey is one of the oldest foods known to humans and being eaten both for its palatability and nutritive value. And the use of honey as a food additive is well known in the art. For example, US Pat. 20060165846 issued to Vladimir Vlad (July 2006) describes a nutritional supplement that combining honey with eggshell powder and crystalizing the mixture in powdered form. Also, Chinese publication No. CN 104472821 (April 2015) describes a hard honey candy and its preparation method.

Honey contains about 69% glucose and fructose that enabling it to be used as a natural sweetener that is better for your overall health than normal white sugar. Honey has anti-bacterial and anti-fungal properties, also, it contains nutraceuticals, which are very effective for the removal of free radicals from the body. As a result, our body immunity is improved against many conditions, even potentially fatal ones like cancer or heart disease.

Honey also contains a variety of vitamins and minerals. Although the type of vitamins and minerals and their quantity depends on the type of flowers used for apiculture, commonly it contains vitamin C, calcium, and iron. Many honey-based confectionary products such as edible chewy bars, chewing gums and the like, jelly-type and jam-like products are commercially available. Other applications including medicinal combination such as wound dressings and so forth are well-known too.

Lemon is a citric fruit that contains the most citric acid, with about 4 g of 100 g of fruit. It is also the finest source of potassium, calcium, iron, vitamin C, B-complex vitamins and bioflavonoids. For example, 100 g lemon contains 88% of vitamin C, 7.5% of iron and 3% of calcium as shown in the USDA National Nutrient database. Because of its sour taste and rich in vitamin C, lemon is usually used for pharmaceutical and confectionary ingredients. Specifically, lemon is used for various treatment methods as described in US Pat. 20020114730 issued to Jazzar (August 2002) and Chinese publication No. CN 105661209 (June 2016).

SUMMARY OF THE INVENTION

In accordance with the present invention, candies, beverages, bars, dietary supplements that contain eggshell powder and at least one additional ingredient selected from the group consisting of organic honey and lemon are disclosed. The natural compositions of this invention can be used as calcium nutrition supplements and food additive required for bone formation and maintenance of healthy bone for adults and children. The composition also can be used for preventing and treating bone loss and metabolic bone diseases such as osteoporosis.

DETAILED DESCRIPTION OF THE PREFERRED EMBODIMENTS

The present invention provides natural compositions that comprise eggshell powder and at least one of the following ingredients: organic honey and lemon. The natural compositions, according to the invention are contemplated to be especially suited for use in the methods for building bone mass and treating or preventing bone loss-related diseases such as osteoporosis.

In order to get a sufficient calcium intake, it is recommended that daily levels of calcium as high as 1000 to 1300 mg per day. However, human body can only absorb a limited amount of calcium at a time. Much of the calcium that is administered in a large single dose may either not be absorbed or may be removed by the kidneys before the body may put it to productive use. So most direct approach to overcome the inability of the body to put large doses of calcium to use all at once is to administer multiple doses of calcium over the course of a day.

According to the suggestion, the calcium absorption in highest in doses is 500 mg and less. For example, someone who takes 1000 mg/day of calcium from supplements might split the dose and take 500 mg at two separate times during the day. See Dietary supplement fact sheets: Calcium, Office of Dietary Supplements, National Institutes of Health. (2011). Thus, the purpose of the present invention is to provide a consistent formulated calcium supplement to a human, which can be employed, for example, as a snack, confectionary product, drink, dietary meal replacement or supplement.

Eggshell powder has a highly effective calcium source; however, it has no attractive taste and smell. So honey and lemon are added to the composition as an active ingredient in order to encourage consumption of this natural composition by children and adult as well as enrich its nutritional fact.

In preferred ingredients of the natural compositions of this invention:
  biological calcium derived from eggshell powder;
  active Manuka honey or any organic honey;
  lemon, lemon juice or lemon extract; and
  other compounds:
    additional ingredients—various vitamins and minerals, milk powder, nuts, oats, fruits and chocolate chips and the like
    flavorings—any natural and artificial flavors including but not limited to fruits, chocolate, cocoa powder, milk and so forth
    coatings—chocolate, carob, coconut, nut, sprinkles and so forth
    food colorings—any suitable coloring may be used According to the invention, the active ingredients included will be the following size amounts per day: about 100 mg to 2000 mg of eggshell calcium, about 200 mg to 2500 mg of honey, and about 100 mg to 1500 mg of lemon. Preferably, the amount of calcium derived from eggshell powder containing in the natural compositions ranges from about 200 mg to about 1300 mg per day. The percentage of honey and lemon in the composition is depending on the desired final product type, texture and so forth.

In preferred embodiment, the natural compositions may include other minerals and vitamins such as vitamin D, B-complex vitamins, folate, some amino acids or any other elements known in the art, that normally stimulate calcium absorption.

The development of natural compositions having satisfactory effect on providing calcium, maintaining healthy bone and/or treating bone loss related disorders without lowering their flavor such as taste, smell and mouth feeling, and being safe even when continually taken, has been further desired.

The composition of the present invention may be formulated for administration to any suitable subject by any suitable form. The formulation for oral use includes candies, beverages, bars, and dietary supplements, which are convenient for all age groups.

Further, the composition can also use in various other food items, including, but without limitation, yogurt, frosting on cakes, granola bars, candy bars, chewing gum, crackers, oat meals, cereal products and the like. The present inventive subject matter also can use in various pharmaceutical applications.

Candies

One preferred embodiment of the present invention may be in the form of candies, which may be mixed together with additional ingredients for making candies. The calcium candies according to the present invention include but are not limited to soft, chewable, coated and uncoated hard candies.

The candies of the present invention are orally administered, and which may include: (a) about 500 mg of 1:2:1 ratio powder of eggshell calcium, honey and lemon; (b) about 400 mg of 1:2:1 ratio powder of eggshell calcium, honey and lemon; (c) about 300 mg of 1:2:1 ratio powder of eggshell calcium, honey and lemon; (d) about 200 mg of 1:2:1 ratio powder of eggshell calcium, honey and lemon; and (e) about 100 mg of 1:2:1 ratio powder of eggshell calcium, honey and lemon.

The candies additionally comprise an effective amount of calcium absorption enhancing agents such as vitamin D, B-complex vitamins and the like. The candies optionally comprise other ingredients, such as milk, orange, vanilla, cranberry, and the like, for enriching nutritional facts and flavor.

In another embodiment, the hard and chewable candies have a pressed tablet and a coating that contains the ranges of active ingredients noted above. Further, the composition can be added into other confectionary products.

Beverages

In another preferred embodiment, the present invention provides a natural composition beverage which is in a liquid, semi-liquid or powder form that is designed to enter into the mouth of a human and be orally consumed, for example, a drink, shake or dry mix.

A natural composition beverage may be in a ready-to-drink liquid form which may consumed without modification, or in a liquid, solid or other concentrate form which can be transformed into a ready-to-drink liquid form with an addition of water or other liquid such as orange juice, apple juice, soymilk, yogurt and so forth.

Preferably, a ready-to-drink liquid composition for an oral administration comprising about 100 to 500 mg of eggshell calcium, about 200 to 1000 mg of honey, about 100 to 500 mg of lemon, and water or other liquid, in an amount that is sufficient to raise the total weight of the nutritional supplement to 100 percent.

Optionally, in addition to the active ingredients mentioned above, one or more vitamins and/or minerals, one or more mouth-feel agents in a combined amount that is providing a desirable mouth-feel, texture or thickness to the nutritional supplements and/or enhancing a mouth-feel, texture or thickness of the nutritional supplements, and/or one or more emulsifiers in a combined amount that is effective for forming or aiding in the formation of, an emulsion, suspending solids within the nutritional supplements and/or emulsifying lipids within the nutritional supplements can be added.

In one embodiment, a beverage concentrate composition contains the ranges of active ingredients noted above, but comprising less liquid component than a ready-to-drink liquid composition is provided. In another embodiment, the composition may be in a form of dry beverage mix.

Nutritional Bars

The present invention also provides a natural composition in the form of a nutritional bar such as chewier bar, hard bar and the like for an administration to a human, comprising the same ingredients and amounts thereof, set forth herein in connection with a ready-to-drink liquid composition, with a few exceptions.

First, in contrast with the ready-to-drink liquid composition, the moisture content of the nutritional bar preferably is about 10 weight percent of the total weight of the nutritional bar or less, and that more preferably ranges from about 4 to about 5 weight percent with a chewier bar generally having a higher moisture content than a hard bar. Most of the water that is present in the ready-to-drink liquid composition, but that are optional, or not included in the nutritional bar can be replaced in the nutritional bar with conventional bar fillers, for example, crisp rice, oatmeal, granola, cereal, dried fruits, nuts, grains, nougats, candy pieces, chocolate, caramel, marshmallow and/or the like, or a wide variety of combinations thereof.

Second, in contrast with the ready-to-drink liquid composition, one or more gums or other mouth-feel agents may, optionally, be included within the nutritional bar in the same amounts, but are not required. However, it is preferred that one or more mouth-feel agents in a combined amount of about 0.1 weight percent of the total weight of the nutritional bar be included therein.

In a preferred embodiment, a nutritional bar contains between about 100 to 500 mg of calcium, between about 200 to 1000 mg of honey, and between about 100 to 500 mg of lemon. In order to provide a daily calcium intake, a nutritional bar can be packaged as a series such as a strip, pack or box.

In one embodiment, a nutritional bar series may comprise a first nutrition bar having 500 mg of calcium, a second nutrition bar having 400 mg of calcium, and a third nutrition bar having 400 mg of calcium in order to provide 1300 mg daily intake of calcium.

In another embodiment, a nutritional bar series may comprise a first nutrition bar having 500 mg of calcium, a second nutrition bar having 400 mg of calcium, and a third nutrition bar having 300 mg of calcium in order to provide 1200 mg daily intake of calcium.

In some embodiments, the nutritional bar series may have only three nutritional bars as described above. But in other embodiments, it may have as many as six or eight bars, each having about 100 to 500 mg of calcium, about 200 to 1000 mg of honey and about 100 to 500 mg of lemon.

Preferred flavorings, colorings or other ingredients such as chocolate chips, nuts, raisins, coconut and so forth may be added. A range of standard food colorings and flavoring products are available in the prior art and may be used with this invention.

A further use of the present composition is in baked goods such as cookies, biscuits, brownie and cakes.

Dietary Supplement of Calcium

The present invention also provides a natural composition in the form of a tablet, capsule, pill or liquid for an administration to a human.

In a preferred embodiment, the composition is in a unit serving dosage form, in particular a compressed unit serving dosage form such as a tablet. A tablet may include but are not limited to molded tablets, chewable tablets, pellets, pills, triturates, hypodermic tablets, effervescent tablets, controlled-release tablets, and immediate release tablets. Tablets may comprise any amount of the eggshell powder according to the invention, but will typically comprise from about 100 mg to about 500 mg of eggshell calcium per a serving dosage form.

In one embodiment, a natural composition of the invention is administered concomitantly with a drug that treats or alleviates a medical disorder precipitated or aggravated by calcium deficiency and/or hypocalcemia such as osteoporosis. Such a composition may be in a form of one or more tablets, in an amount providing about 300 to about 2000 mg calcium per day.

Preferably, the eggshell calcium supplements will also contain honey. Typically, the supplement will comprise at least about 200 mg of honey, preferably, at least about 300 mg of honey, at least about 400 mg, at least about 500 mg, at least about 600 mg, and may range upwards of about 1000 mg, about 2000 mg, about 2500 mg of honey.

Preferably, the eggshell calcium supplements will also contain lemon. Typically, the supplement will comprise at least about 100 mg of lemon (citric acid), preferably, at least 200 mg of lemon, at least about 300 mg, at least about 400 mg, at least about 500 mg, and may range upwards of about 800 mg, about 1000 mg, about 1500 mg of lemon.

The natural composition may also be a single administration daily dosage form for a full day's supply of calcium. Various methods are known in the pharmaceutical industry for providing extended or extended release of pharmaceutical actives. These methods are, for the most part, based on associating the pharmaceutical material with another material that reacts differently to the acidic environment of the stomach and the more basic environment of the small intestine. The compressed tablets made from these materials may be coated or uncoated. The coating materials may also be designed to delay release of the coated material that may or may not contain calcium as appropriate for the use of the formulation.

Thus, in various embodiments, the calcium supplement tablets will comprise at least 100 mg, at least 200 mg, at least 300 mg, at least 400 mg, at least 500 mg, at least 600 mg, at least 700 mg, at least 800 mg, at least 900 mg, at least 1000 mg, at least 1100 mg, at least 1200 mg, or at least 1300 mg, and may range upwards of about 1500 mg, about 1800 mg, about 2000 mg of eggshell calcium according to the invention.

In another embodiment of the composition, the active ingredients are formulated into a dietary supplement in the form of ingestible capsules, which also contain the ranges of active ingredient noted above.

In certain embodiments, the active ingredients may be delivered in a soft or hard gel capsule by mixing the active ingredient with water or oil such as peanut oil, or olive oil and enclosing the resulting formulation in a capsule.

The calcium supplement tablet may comprise any additional ingredients known to one skilled in the art, including pharmaceutically or nutraceutically acceptable excipients, for example, carriers, diluents, disintegrants, lubricants, flavorants, and the like.

A wide variety of vitamins and minerals may be included in, or used to prepare, the natural composition of the invention in varying quantities. In addition to the vitamins and minerals that are otherwise described herein, other vitamins and/or minerals that may be included in the natural composition of the invention include, for example, vitamin B1, vitamin B2, vitamin B3, vitamin B6, vitamin B12, vitamin D, vitamin K, folacin, niacinamide, iron, phosphorus, pantothenic acid, iodine, magnesium, zinc, selenium, copper, manganese, molybdenum, choline, fluoride, chloride, biotin and various mixtures or other combinations thereof. Vitamins and minerals are commercially available from sources known by those of skilled in the art, such as Hoffmann-LaRoche Inc. (Nutley, N.J.).

Compounds that provide flavor (flavorings or flavor agents), which may be used in the natural composition include those flavors known to the skilled artisan, such as natural and artificial flavors. These flavorings may be chosen from synthetic flavor oils, flavoring aromatics and/or oils, oleoresins and extracts derived from plants, leaves, flowers, fruits, and so forth, and combinations thereof. Preferably, natural fruit flavors such as orange, apple, strawberry, raspberry, cherry, mango, pomegranate, pineapple, banana and so forth. Other potential flavors include a milk, cheese, cream, yogurt, vanilla, cinnamon, cocoa, chocolate, and coffee. These flavoring agents may be used in liquid or solid form and may be used individually or in admixture.

The invention having been described by the foregoing description of the preferred embodiments, it will be understood that the skilled artisan may make modifications and variations of these embodiments without departing from the spirit or scope of the invention as set forth in the following claims:

What is claimed is:

1. A natural composition for increasing bone mass growth and treating bone loss related diseases, consisting of:
    about 100 mg to 1300 mg of biological calcium derived from eggshell powder;
    about 200 mg to 1000 mg of an organic honey or honey mixed other bee products selected from the group consisting of flower pollen, bee bread, propolis and a mixture thereof, and wherein the organic honey in any form selected from the group consisting of creamed, crystallized, dried or liquid and a mixture thereof;
    about 100 mg to 500 mg of lemon in a form of a liquid or powder; and
    an effective amount of two or more other components selected from the group consisting of milk, nuts, oats, vanilla, fruit, chocolate chips, vitamins, minerals, flavoring and coloring substance selected from the group consisting of fruit flavors, botanical flavors and a mixture thereof depending on a desired final product selected from the group consisting of candies, beverages, nutritional bars and dietary supplements.

2. The composition as defined in claim 1, wherein said composition is orally administered once or more times a day.

3. The composition as defined in claim 1, wherein said amount of eggshell calcium ranges from about 100 mg to 1300 mg per day, or ranges from about 100 mg to 500 mg per serving dosage.

4. The composition as defined in claim 1, wherein said organic honey is a pure honey.

5. The composition as defined in claim 1, wherein said lemon is extracted from lemons, lemon seeds, lemon pulp, lemon rind, zest and a mixture thereof.

6. The composition as defined in claim 1, wherein said other components are selected from the group consisting of milk, nuts, oats, vanilla, fruit, chocolate chips and a mixture thereof that are for enriching nutritional facts and flavor of the natural compositions.

7. The composition as defined in claim 1, wherein said other components are one or more vitamins, minerals or vitamins and minerals in an amount that is safe for consumption by humans, and wherein said components are effective for providing a nutritional, medical or other health benefit to the human or for enhancing the calcium absorption and general nutrition of the human.

8. The composition as defined in claim 1, wherein said other components are one or more flavoring and coloring substance selected from the group consisting of fruit flavors, botanical flavors and a mixture thereof.

9. A natural composition for increasing bone mass growth and treating bone loss related diseases consisting of biological calcium derived from eggshell powder, organic honey and lemon in a ratio of 1:2:1, wherein the amount of calcium ranges from about 100 mg to 1300 mg and optionally further consisting of an additional ingredient selected from the group consisting of water, milk, orange juice, apple juice, soymilk, yogurt, nuts, oats, grains, raisins, coconut, vanilla, fruit, chocolate chips, vitamins, minerals, flavoring and coloring substance selected from the group consisting of fruit flavors, botanical flavors, pharmaceutically or neutraceutically acceptable carriers, diluents, disintegrants, lubricants, and a mixture thereof which are depending on a desired final product selected from the group consisting of candies, beverages, nutritional bars, and dietary supplements.

10. The composition as defined in claim 9, wherein said candies are soft, chewable, coated and uncoated hard candies consisting of about 100 mg to 500 mg of eggshell calcium in the total candy, about 200 mg to 1000 mg of honey in the total candy and about 100 mg to 500 mg of lemon in the total candy.

11. The composition as defined in claim 9, wherein said beverages are a ready-to-drink composition or a beverage concentrate composition consisting of about 100 mg to 500 mg of eggshell calcium, about 200 mg to 1000 mg of honey, about 100 mg to 500 mg of lemon, and water or other liquid selected from the group consisting of milk, orange juice, apple juice, soymilk and yogurt that is sufficient to raise the total weight of the beverage composition to 100 percent.

12. The composition as defined in claim 11, wherein said water or other liquid selected from the group consisting of milk, orange juice, apple juice, soymilk and yogurt in the beverage ranges from about 30% by weight to about 70% by weight in a ready-to-drink composition, from about 5% by weight to about 20% by weight in a beverage concentrate composition.

13. The composition as defined in claim 11, wherein said water or other liquid is orange juice, apple juice, milk, soymilk, yogurt and/or a mixture thereof.

14. The composition as defined in claim 11, wherein said beverage composition is a dry beverage mix composition.

15. The composition as defined in claim 9, wherein said nutritional bars are in the form of one or more bars consisting of biological calcium derived from eggshell powder, organic honey and lemon in a ratio of 1:2:1, wherein the total weight of eggshell calcium ranges from about 100 mg to about 500 mg per bar.

16. The composition as defined in claim 15, wherein said nutritional bar kit comprises a series of bars packaged together in a strip, a pack or a box, wherein the kit provides a sufficient number of bars to result in a total weight of between about 700 mg to 1300 mg calcium.

17. The composition as defined in claim 15, wherein said optional additional ingredient is selected from the group consisting of nuts, oats, grains, raisins, chocolate, coconut and a mixture thereof.

18. The composition as defined in claim 9, wherein said dietary supplements are in solid form selected from the group consisting of tablets, pills and/or in liquid form selected from the group consisting of capsule and drink that consisting of biological calcium derived from eggshell powder, organic honey and lemon in a ratio of 1:2:1, wherein the amount of calcium ranges from about 100 mg to 1300 mg.

19. The composition as defined in claim 18, wherein said optional additional ingredient is selected from the group consisting of pharmaceutically or neutraceutically acceptable carriers, diluents, disintegrants, lubricants, flavorants, and a mixture thereof.

20. A natural composition consisting of biological calcium derived from eggshell powder, organic honey and lemon in a ratio of 1:2:1, wherein the amount of calcium ranges from about 100 mg to 1300 mg.

* * * * *